United States Patent [19]

Andrade et al.

[11] Patent Number: 5,135,876
[45] Date of Patent: Aug. 4, 1992

[54] METHOD AND APPARATUS FOR THE REGULATION OF COMPLEX BINDING

[75] Inventors: Joseph D. Andrade; James Herron, both of Salt Lake City, Utah

[73] Assignee: University of Utah

[21] Appl. No.: 100,935

[22] Filed: Sep. 24, 1987

[51] Int. Cl.$^5$ .................. G01N 33/536; G01N 33/543
[52] U.S. Cl. ...................... 436/518; 436/527; 436/536; 436/805; 422/82.05; 422/82.08; 422/82.11
[58] Field of Search ............... 436/527, 805, 806, 807, 436/824, 825, 512, 518, 524, 536, 164, 172; 422/57, 58, 68.1, 82.05, 82.08, 82.09, 82.11; 204/15, 402, 403; 385/12, 129-131; 250/362, 363.01, 458.1, 459.1, 472.1, 473.1

[56] References Cited

U.S. PATENT DOCUMENTS

| | | | |
|---|---|---|---|
| 3,992,631 | 11/1976 | Harte | 250/365 |
| 4,144,452 | 3/1979 | Harte | 250/302 |
| 4,157,871 | 6/1979 | Anderson et al. | 356/341 |
| 4,219,539 | 8/1980 | Deutsch | 424/8 |
| 4,240,751 | 12/1980 | Linnecke et al. | 356/409 |
| 4,368,047 | 1/1983 | Andrade et al. | 436/805 |
| 4,447,546 | 5/1984 | Hirschfeld | 436/527 |
| 4,558,014 | 12/1985 | Hirschfeld et al. | 436/527 |
| 4,582,809 | 4/1986 | Block et al. | 436/527 |

FOREIGN PATENT DOCUMENTS 0103426 8/1983 European Pat. Off. .

OTHER PUBLICATIONS

Erlanger, "Photoregulation of Biologically Active Macromolecules", Annual Review of Biochemistry, vol. 45, 1976, pp. 267-283.

Herron et al., "Thermodynamic Properties of Ligand Binding by Monoclonal Anti-Fluorescyl Antibodies", Biochemistry, vol. 25, 1986, pp. 4602-4609.

J. D. Andrade, J-N Lin, J. Herron, M. Reichert, and J. Kopecek, "Fiber Optic Immunodetectors: Sensors or Dosimeters?" SPIE vol. 718, Fiber Optic and Laser Sensors IV (1986) first published Apr. 1987.

V. Hlady, D. R. Reinecke, and J. D. Andrade, "Fluorescence of Adsorbed Protein Layers", Journal of Colloid and Interface Science, vol. III, No. 2, Jun. 1986.

K. Newby, W. M. Reichert, J. D. Andrade, and R. E. Benner, "Remote Spectroscopic Sensing of Chemical Adsorption Using a Single Multimode Optical Fiber", Applied Apitcs, vol. 23, No. 11, Jun. 1, 1984.

Andrade, Van Wagenen et al. "Remote Fiber-Optic Biosensors Based on Evanescent-Excited Fluoro-Immunoassay: Concept and Progress" IEEE Transactions on Electron Devices, vol. Ed-32, No. 7, pp. 1175-1179, Jul. 1985.

Kranz, Herron et al., "Mechanisms of Ligand Binding by Monoclonal Anti-fluorescyl Antibodies" Journal of Biological Chemistry, pp. 6987-6995 Jun. 1982.

Newby, Andrade et al. "Remote Sensing of Protein Absorption Using a Single Optical Fiber" Journal of Colloid and Interface Science, vol. 111, No. 1, pp. 280-282, May 1986.

Primary Examiner—Robert J. Warden
Assistant Examiner—William A. Beisner
Attorney, Agent, or Firm—Trask, Britt & Rossa

[57] ABSTRACT

A reusable biosensor is disclosed. A molecule containing a moiety of an antibody-antigen complex and photosensitive polymers are bonded to an optical conduit. When placed in a solution, the presence or absence of a second complementary moiety of an antibody-antigen complex can be determined by sensing whether or not the first moiety is complexed. The first moiety of an antibody-antigen complex can then be regenerated by transmitting light through the optical conduit which alters the structure of the photosensitive polymers to cause interference with said complex, thereby dissociating the second complementary moiety from the first moiety. The ability to regulate and control specific binding has applications can be useful in information storage devices, bioorganic electronic devices, and optical devices.

33 Claims, 1 Drawing Sheet

METHOD AND APPARATUS FOR THE REGULATION OF COMPLEX BINDING

FIELD

This invention relates to devices and methods for the detection of predetermined substances capable of being bound specifically to a high affinity binding agent.

BACKGROUND

An "antigen" (Ag) is any substance that will provoke an immune response. In general, antigens are considered greater than 10,000 in molecular weight and are proteins, carbohydrates or glycoproteins. Smaller, less rigid molecules are not normally antigenic in pure form, but can be made so by linking them to larger molecules. These smaller molecules are called "haptens."

Antibodies ("Ab") are immunoglobulin molecules (serum proteins) of which there are several classes. Each class has its own characteristic molecular size, electrophoretic migration velocity, carbohydrate content, etc.

Antibodies can be broken into fragments, the Fab fragment and the Fc fragment. The Fab fragment, like intact antibodies, can bind antigenic substances (e.g. haptens and antigens).

For purposes of this disclosure, a "ligand" is any chemical compound the presence or absence of which can be determined by the use of a chemical assay. With such a definition, a ligand may be an antigen, a hapten, an antibody, an antibody fragment, chemicals which can react with a cell receptor (e.g. acetylcholine), an enzyme, chelatable metals, lectins, etc. Through a chemical assay, ligands complex with some complementary chemical receptor (e.g. an antibody will bind to a specific antigen) and can then be examined to determine the presence, absence, or quantity of the ligands.

Specific chemical assay in complex mixtures generally depends on the use of specific, high affinity binding agents. These high affinity agents, e.g. antibodies, membrane receptors, enzymes, lectins, or chelates, have high binding constants. Generally, the greater the binding constant of the binding agent, the greater the chemical assay's ultimate sensitivity. Such assays are "one-shot" measurements. In the case of an immunoassay, one takes a sample, mixes the reagents, takes a reading, and discards everything. W. P. Collins, editor, *Alternative Immunoassays*, Wiley, 1985.

Considerable interest exists in developing specific chemical sensors, i.e. detectors which respond to changes in concentration of a specific chemical—either continuously or at least semi-continuously. Andrade, Van Wagenen, et al. "Remote Fiber-Optic Biosensors Based on Evanescent-Excited Fluoro-Immunoassay: Concept and Progress," *IEEE Trans. Elect. Dev.*, p. 1175-1179, 1985. In building such a device, a high binding constant for maximal sensitivity is desired, but a fast response time is also needed to permit continuous or semi-continuous measurements. Means for decreasing the binding constant between the reagents between measurements would be desirable. Ideally, one would "zero" the sensor between measurements and still measure the solution often enough to have a nearly continuous readout. Andrade, Van Wagenan, et al., supra. Finally, a sensor having the maximum possible dynamic range would be preferred.

The aforementioned characteristics, i.e. high binding constant, fast response time, and means for decreasing the binding constant between measurements are generally considered mutually exclusive, absent regulation of the binding constant. Andrade, Lin, et al., "Fiber Optic Immunodetectors: Sensors or Dosimeters?" *SPIE* 718 (1986) 280.

The high binding constants of the high affinity binding agents give them their exquisite sensitivity, but also render them with a very slow dissociation rate. Pecht, "Dynamic Aspects of Antibody Function," in M. Sela, editor, *The Antigens*, Vol. 6, Academic Press, 1982, page 1. Systems using such agents are in effect dosimeters rather than sensors due to this slow dissociation rate. To reuse these systems some means to weaken the bond between the binding agent (i.e. chemical receptor) and the antigenic substance (i.e. ligand) is needed to permit the complex to dissociate within a reasonable time. Andrade, Lin, et al., supra, and Lin and Schultz, *IEEE Trans. Biomed. Eng.* BME-33 (1986) 133.

In the case of membrane receptors for biochemicals (e.g. toxins and drugs), the ligand-receptor complex is often internalized or otherwise "turned over." Regeneration of the membrane surface in such a manner requires complex synthetic machinery which is presently impractical for man-made remote sensors.

Heretofore, the standard means to dissociate antigen-antibody (Ag-Ab) complexes is to induce a significant conformational change in Ag, Ab, or both by drastic changes in the local solution environment. These changes include radically altering the pH (e.g. to pH 2-3 or pH 11); adding to the tested solution a high concentration of chaotropic salts or a high concentration of agents which diminish hydrophobic interactions; or radically changing the temperature. Walters, "Affinity Chromatography," *Anal. Chem.* 57 (1985) 1099A; Parikh and Cuatrecasas, "Affinity Chromatography," *Chem. Eng. News*, (Aug. 26, 1985) 17; Pecht, supra; Goding, *Monoclonal Antibodies*, Academic Press, 1983, pp. 199-203.

Unfortunately, such treatments often lead to irreversible conformational changes which destroy the desired specific binding properties of the binding agent. Goding, supra.

In addition, it is difficult to deliver the necessary eluting agents (e.g. acids, bases or salts) on command to a remote sensor site. A different approach is to use low affinity antibodies, this approach also results in low sensitivity. Another method is to use special monoclonal antibodies with a binding site structure very susceptible to moderate changes in local pH. Hill, "Switch Immunoaffinity Chromatography with Monoclonal Antibodies," *Biotechniques* (1984) 14.

The high binding affinities of antibodies can lead to an almost irreversible binding of ligands to the antibodies. A need exists for a method of removing specifically bound ligands from a sensor surface without the use of damaging eluting agents. In vivo, a protein-ligand complex is usually broken down by proteolysis. In immunoassays and affinity chromatography applications, it is usually necessary to dissociate the protein-ligand complex without denaturing the protein. Thus, the dissociation of the protein-ligand complex is a fundamental problem in both basic and applied research. It would be desirable to modulate the affinity of the protein in a predictable and reversible manner.

The ability to regulate ligand-receptor binding constants would be of major significance in the development of (a) effective specific binding sensors with optimal sensitivity, response time, and dynamic range, (b) better molecular separation processes as compared to the prior art, and (c) better understanding and control of a wide range of biological and medical processes.

Certain "sensors" are described in the following patents:

U.S. Pat. No. 4,582,809 to Block, et al. discloses a method and apparatus for fluorescent immunoassay which utilizes total internal reflection to produce an evanescent wave in the liquid base. An optical fiber is provided with a plurality of coupling sites to which may be bound haptens, antigens, antibodies, and antibody fragments for reaction with a liquid to be assayed.

U.S. Pat. No. 4,558,014 to Hirschfeld, et al, discloses an apparatus and method similar to Block, et al., with "moieties of an antibody-antigen complex" (e.g. haptens, antigens, antibodies and antibody fragments.)

EPO 103 426 AZ to Hirschfeld discloses an immunoassay apparatus and method consisting of a short length of precise diameter capillary tubing having an axially disposed optical fiber to which is immobilized a monolayer of a moiety of an antibody-antigen complex, an inert diluent, and a preload of a known amount of tagged complement to the immobilized component.

SUMMARY OF THE INVENTION

The invention comprises an actuatable coupling-decoupling device which can be used to regulate and detect ligand-receptor binding optically by selected energy signals, especially transmitted signals. Also disclosed is a probe element for use in a coupling-decoupling device.

The actuatable chemical coupling-decoupling device of the present invention comprises: 1) a substrate capable of conducting an energy signal; 2) a plurality of first pendant molecules, each molecule being attached to said substrate at a proximal end, and each having a coupling group (or "complexing site") at a free distal end, said coupling groups are capable of selectively coupling to chemical compounds ("ligands") having a chemical structure capable of coupling to said coupling groups; 3) a plurality of second pendant molecules, each being attached at its proximal end to said first conductive substrate, in proximity to said plurality of first pendant molecules, said second pendant molecules having at least two conformations, a first contracted conformation existing when insufficient energy is conducted through said conductive substrate to exceed the threshold energy required to extend said second pendant molecules, and a second extended conformation when said second pendant molecules are subjected to an energy signal sufficiently greater than the threshold energy for that particular molecule to extend said second pendant molecules from said first contracted conformation (or "state") to their second extended conformation such that the distal ends of said second pendant molecules extend proximate to said coupling groups of said first pendant molecules; 4) sensing means for determining the coupling of a coupling group of a first pendant molecule to a chemical compound having a site capable of coupling to said coupling group of a first pendant molecule; and 5) activation means attached to said conductive substrate to activate said second pendant molecules to said extended state thereby decoupling said coupled chemical compound from said coupling site of said first pendant molecule.

A probe element for an actuatable chemical coupling-decoupling device may comprise: a conductive substrate capable of conducting an energy signal; a plurality of first pendant molecules, each molecule being attached to said substrate at a proximal end, and having a coupling group (or "complexing site") at a free distal end, said coupling groups capable of selectively coupling to chemical compounds having a chemical structure capable of coupling to said coupling groups; and a plurality of second pendant molecules each being attached at its proximal end to said conductive substrate and in proximity to said plurality of first pendant molecules, said second pendant molecules having two conformations, a first contracted conformation existing when no energy is conducted through said conductive substrate, and a second extended conformation existing when second pendant molecules are subjected to an energy signal to extend said second pendant molecules from said first contracted conformation to their second extended conformation, such that the distal ends of said second pendant molecules extend proximate to said coupling groups of said first pendant molecules.

Many of the elements of both the actuatable chemical coupling-decoupling device and the probe element of the actuatable chemical coupling-decoupling device are identical. In both, the first pendant molecules may be attached physically, e.g. by adsorption, or chemically, e.g. by covalent bonding, to the substrate. Also, the energy signal conducted through the substrate may be electromagnetic in nature, e.g. a wave of light. If light is the energy conducted through the conductive substrate, the second pendant molecules comprise photosensitive polymers. Substrates capable of conducting light include planar waveguides and optical fibers.

In an alternative embodiment, the substrate is an electrical conductor, in which case, the energy signal comprises electrical energy and said second pendant molecules are electro-stimulated polymers. In another alternative embodiment, the substrate is a thermally conductive substance, the energy signals consist of heat energy, and the second pendant molecules are thermally stimulated to extend from the natural, i.e. unenergized, contracted to an extended condition.

Another alternative embodiment is to transmit light energy which is then transformed to heat energy at the interface, thereby producing the heat energy locally.

In both the probe element and the actuatable chemical coupling-decoupling device, the first pendant molecules may comprise a membrane receptor (e.g. the acetylcholine receptor "AChR") a moiety of an antibody-antigen complex, for example a hapten, antigen, antibody, or antibody fragment (Fab), an enzyme, a lectin, a chelate or other specific binding agent.

Also, in both the probe element and the actuatable chemical coupling-decoupling device, the second pendant molecules may be attached either physically or chemically to the conductive substrate. It is preferable, however, to have their proximal ends of the second pendant molecules covalently bonded to the conductive substrate or chemically bonded to the first pendant molecules at a location remote from the distal end of said first pendant molecules.

A method for externally regulating ligand-receptor binding comprises: 1) passing a ligand containing solution over a sensor comprising: a) an optical conduit, b) receptor molecules having a complexing site bonded to said optical conduit at an end distal to said complexing site, and c) photoexpansive polymers bonded to said optical conduit interspersed between said receptor molecules so that in a first conformation of the photoexpansive polymers said ligands complex with the complexing site of said receptor molecules; and 2) transmitting light through said optical conduit thereby expanding said photo-expansive polymers to extend proximate said complexing sites of said receptor molecules, thereby dissociating said ligands from said receptor molecules.

BRIEF DESCRIPTION OF THE DRAWING

In the drawings, which illustrate various methods for carrying out the invention.

Figure 1:
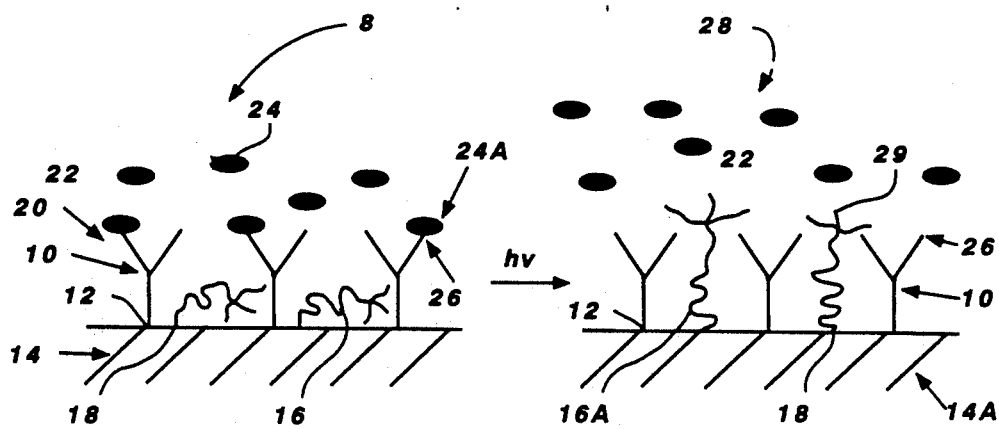
FIG. 1 is a stylized view of an embodiment of the invention, illustrating a photo-induced coil expansion of the second pendant molecules, thus altering the binding of the antigen-antibody binding sites.

FIG. 3 is a stylized view of one embodiment of the present invention wherein the first pendant molecules are bonded to the conductive substrate by a hydrophilic tether, and the energy signal consists of heat energy (or a thermal pulse) transmitted through the conductive substrate.

DETAILED DESCRIPTION OF THE PREFERRED EMBODIMENTS

The conductive substrate of the present invention is a substance capable of conducting an energy signal, and to which may be bonded, or otherwise attached, certain chemical compounds. Electrical energy, magnetic waves, light, and heat are all energy signals envisioned as being conducted or transmitted through the substrate. The substrate, of course, must be compatible with its environment as part of a probe or sensor.

The composition of the conductive substrate varies according to the particular energy signal to be conducted. If the energy signal to be conducted through the conductive substrate is electrical energy, then the conductive substrate will be electrically conductive (e.g. a conductive metal such as copper, aluminum and the like, or carbon, usually graphite). If the energy signal conducted through the conductive substrate is heat energy, then the conductive substrate will be made of a thermally conductive substance (e.g. a metal such as aluminum, copper and the like).

In a preferred embodiment, the energy signal to be conducted is light, which for the purpose of this invention includes infrared and ultraviolet as well as visible light, although visible light waves are preferred. The conductive substrate in the case of light as the energy signal may be any quartz, silica or other material (e.g. polymer) capable of efficiently transmitting light. Typical light conductive substrates are optical conduits (e.g. optical fibers, planar waveguides and the like). Such optical materials are especially inert to the various liquid systems to which they are exposed as a probe.

If an optical fiber is to be used with the invention, it may first be prepared to minimize attenuation of the evanescent field in order to minimize loss and maximize optical transmission. A commercial optical fiber consists of a like core, surrounded by a lower refractive index "cladding," and a protective outer coating. To prepare the optical fiber for the purpose of the invention, the cladding and coating are removed from the sensing region of the optical fiber, thereby providing a conduit/sensor which evanescently interacts with the surrounding medium, such medium typically being a liquid or gas system containing various chemical compounds. An optical fiber useful as a conduit/sensor is disclosed in Andrade, Van Wagenen, et al. "Remote Fiber-Optic Biosensors Based on Evanescent-Excited Fluoroimmunoassay: Concept and Progress," *IEEE Transactions on Electron Devices*, 1175–1179, 1985, the contents of which are hereby incorporated by reference.

The first pendant molecules of the present invention are binding agents which may comprise one moiety of an antibody-antigen complex, a receptor, a chelate, a lectin, or some other molecule capable of specifically binding to a specific substance. The choice of which binding agent to use for the first pendant molecules is dependent upon the particular ligand in solution to be assayed. If the ligand to be assayed is an antibody (e.g. HIV), then the first pendant molecules would comprise an antigen or hapten capable of specifically binding to that particular antibody (i.e. a complementary moiety of the antibody-antigen complex for the particular ligand). If the ligand to be assayed were a receptor/ligand (e.g. acetylcholine), then the first pendant molecule could be a cell receptor receptive to that particular ligand (e.g. AChR). The first pendant molecule could also be a chelating agent if the ligand were a metal or other ion. Preferred first pendant molecules are those which may be readily attached to a conductive substrate, e.g. an optical sensor, and are very selective as to ligands with which it will react.

The first pendant molecules have complexing sites ("coupling groups") which react or bond with the assayed ligands. High affinity binding agents are preferred first pendant molecules due to their high selectivity for a chosen ligand. This high selectivity decreases the chance of obtaining a false positive test when the first pendant molecules are sensed to determine if any components of the tested solution are the chosen ligand.

In a preferred embodiment, the conductive substrate is an optical conduit, the energy signal is light, and the first pendant molecule is a moiety of antibody-antigen complex. In this case, the moiety to be attached to the optical conduit can be covalently bonded or linked to the surface of the optical conduit. Some techniques for binding antigens and antibodies to an optical conduit are disclosed in Hirchfeld, et al., U.S. Pat. No. 4,558,014 and U.S. Pat. No. 3,652,761 to Weetall, and are known to those skilled in the art, the contents of these patents are hereby incorporated by this reference. Other techniques for attaching the first pendant molecules to the conductive substrate are disclosed in Lowe, et al., *Affinity Chromatography*, New York, Wiley 1974, which is incorporated by reference.

The second pendant molecules of the present invention are typically polymers which "expand" or increase in length in the presence or absence of an energy signal which is to be conducted through the conductive substrate. These second pendant molecules have a distal and a proximal end. These molecules are bonded or otherwise attached to the conductive substrate at their proximal end. In an alternative embodiment, the second pendant molecules are bonded at their proximal ends (FIG. 2) to the first pendant molecules. The distal ends of the second proximal molecules are free and not bonded or otherwise attached to the conductive substrate or first pendant molecules. These distal ends may have side chains (or "fingers") of their own which increase their efficiency in dissociating the ligands from the first pendant molecules.

The second pendant molecules exist in at least two different conformations. The first conformation is a contracted conformation; the second pendant molecules may exist in this conformation when no threshold energy signal is conducted through the conductive substrate. In other second pendant molecules, the second pendant molecules contract in the presence of the threshold energy signal. A threshold energy signal is that energy signal selected for the particular embodiment of the invention which is at a level sufficient to initiate extension or contraction of the second pendant molecules. Depending on the specific coil expansion/contraction mechanism, which is related to the specific chemistry of the molecule, the applied specific energy may enhance or stabilize the contracted state *or* the extended state of the molecule. In the contracted conformation, the second pendant molecules are of such a foreshortened length that their free distal ends do not interfere with the complexing site of the first pendant molecules or with the ligands' interaction with these complexing sites (FIG. 1). When an energy signal (e.g. light) exceeding the threshold energy level is transmitted through the conductive substrate, the structure of the second pendant molecules alters to an the chosen conformation. In the extended conformation, the distal ends of the second pendant molecules are thought to interfere with the complexing site of the first pendant molecules and/or the interaction of the ligand with the complexing site and thereby cause the ligands to dissociate from the complexing sites of the first pendant molecules. The "interference" need not be solely "mechanical" or steric but may be thermodynamic in nature. The presence of the extended polymer affects the local thermodynamic equilibrium, thereby changing the binding.

Figure 2:
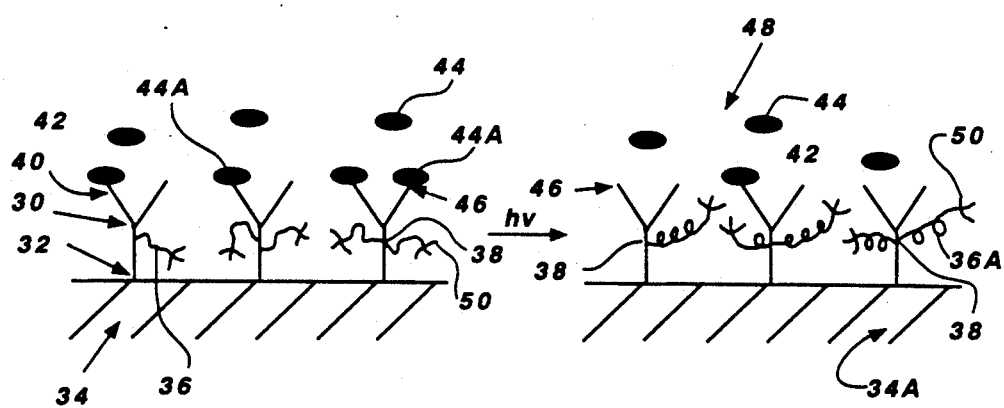
FIG. 2 is a stylized view of one embodiment of the invention, wherein the second pendant molecules (photosensitive polymers) are directly bonded to the first pendant molecules (antibodies).

The second pendant molecules preferably are covalently bonded to the conductive substrate in much the same way as the aforementioned first pendant molecules. In an alternative embodiment, the second pendant molecules are covalently bonded directly to the first pendant molecules (FIG. 2). These molecules may also have their proximal ends embedded in a coating on said substrate. If the conductive substance is an optical conduit, preferring coatings would have a refractive index identical to that of the optical conduit.

In a preferred embodiment, the second pendant molecules are polymers which undergo photoisomerization. Well known photoisomerizable polymers typically contain an azobenzene moiety. Molecules which undergo photoisomerization are disclosed in Ross, et al. "Photochromism by Cis-Trans Isomerization," in G. H. Brown (ed.) *Photochromism*, Wiley, 1971 and Erlangen, "Photoregulation of Biologically Active Macromolecules," *Ann. Rev. Biochem.* 45 (1976) 267-283. These photoisomerizable polymers are "photoexpansive" (i.e. expand in the presence of light), and may contain the aforementioned azobenzene or a stilbene moieties in their structure. The change in conformation of these moieties from "cis" (i.e. contracted) to "trans-" (i.e. extended) in the presence of a threshold amount of light appears to stimulate the length increase in these polymers. Because of this length increase, such second pendant molecules having a length in their extended conformation slightly longer than that of the chosen first pendant molecule are preferred. Ishihara, *Makro Mol. Chem. Rapid Comm.*, Vol. 5, 1984.

Typical second pendant molecules would be a copolymer containing methacrylate, acrylic acid and azobenzene moieties.

Sensing means for determining the presence or absence of a complexed moiety on the substrate are known in the art. Typical sensing means are total internal reflection fluorescence (TIRF), use of a separate optical conduit proximate the conductive substrate, use of a tag, etc. Some such sensing means are disclosed in Newby, et al., "Remote Sensing of Protein Adsorption Using a Single Optical Fiber," *Journal of Colloid and Interface Science*, Vol. 111, No. 1, May 1986, pages 280-282, the contents of which are hereby incorporated by reference.

Activation means would include a suitable light source if the energy signal is a light wave; an electrical source if the energy signal is electrical; and a suitable generator if the energy signal is to be a thermal pulse (e.g. a infrared light source for optical conduit or electricity for resistance heating of the conductive substrate). The source is external the conductive substrate and is preferably easily controllable by a user.

When the activation means is a light source, it provides optical radiation of the proper frequency chosen on the basis of any particular tags used by the sensing means. Wavelengths of light appropriate to extend (or contract) the conformation of the photoisomerizable second pendant molecules should also be generatable by the light source.

Referring now to the figures, FIG. 1 depicts a sensor 8, in which first pendant molecules 10 in this case the antibody Immunoglobin G (IgG) against digoxyn are covalently bonded at their proximal ends 12 to the conductive substrate 14. In the embodiment depicted in FIG. 1, the conductive substrate 14 is an optical conduit (e.g. an optical fiber or a planar waveguide). Second pendant molecules 16, in this case polyethyl methacrylate copolymerized with phenylazodenzoyloxy ethyl methacrylate are also shown, and in the left half of FIG. 1, they are depicted in their contracted conformation. The second pendant molecules 16 are bonded to the conductive substrate 14 at their proximal end 18. The first pendant molecules 10 are shown with their distal ends 20 extending into a surrounding ligand containing solution 22. The ligands 24, in the depicted case digoxyn, depicted floating in the surrounding ligand containing solution 22. Certain ligands 24A are depicted as complexed with the first pendant molecules 10 at the first pendant molecules' complexing sites 26. No light (hv) or other chosen energy signal is being conducted through the conductive substrate 14 in the left half of FIG. 1.

In the right half of FIG. 1, generally 28, light (hv) is being transmitted through the energy conductive substrate 14A, and the second pendant molecules are now in their extended conformation 16A. The distal ends 29 of the second pendant molecules are now distal from the conductive substrate 14A, and are in close proximity to the complexing sites 26 of the first pendant molecules 10. The ligands 24 are thereby dissociated from the first pendant molecules 10 and are free to complex with the complexing sites 26 again. In essence, the sensor depicted in FIG. 1 is recharged and ready for reuse. When the energy signal (i.e. light) is no longer conducted through the conductive substrate 14, the ligands 24 may rebind to the first pendant molecules 10.

Of course, the solution 22 can be changed during the time when the second pendant molecules are in their extended conformation 16A and the ligands 24 are dissociated from the first pendant molecules 10. This solution change can be used to cleanse the sensor 8.

In FIG. 2, another embodiment of reusable sensor is depicted. First pendant molecules 30 (e.g. anti-fluorescyl antibodies) are attached at their proximal ends 32 to the conductive substrate 34. In the embodiment depicted in FIG. 2, the conductive substrate 34 is also an optical conduit. Second pendant molecules 36 are shown in their contracted conformation in the left half of FIG. 2. The left half of all of the figures depicts a no chosen energy condition of the substrates 14, 34, 54 (i.e. the chosen or threshold energy signal is not being conducted through the conductive substrate at the time depicted). The second pendant molecules 36 are bonded at their proximal and 38 directly to the first pendant molecules 30.

The first pendant molecules 30 are shown with their distal ends 40 extending into the surrounding ligand containing solution 42. The ligands 44, in the depicted case fluorescein, are depicted as free floating in the surrounding solution 42. Certain ligands 44A are depicted as complexed with the first pendant molecules 30 at the first pendant molecules' complexing sites 46. No light (hv) or other chosen energy signal is being conducted through the conductive substrate 34 in the left half of FIG. 2.

In the right half of FIG. 2, generally 48, light (hv) is being transmitted through the conductive substrate 34A, and the second pendant molecules are in their extended conformation 36A. The distal ends of the second pendant molecules are now proximal the complexing sites 46 of the first pendant molecules 30.

The distal ends 50 of the now extended second pendant molecules 36A interact with, or otherwise dissociate the ligands 44 from the complexing sites 46. The ligands 44 are then free floating in the surrounding solution 42. When the chosen energy signal is no longer conducted through the conductive substrate 34, the ligands 44 may rebind to the first pendant molecules 30.

As in the embodiment depicted in FIG. 1, the solution 42 can be changed when the ligands 44 are dissociated from the first pendant molecules 30 to cleanse the sensor.

Figure 3:
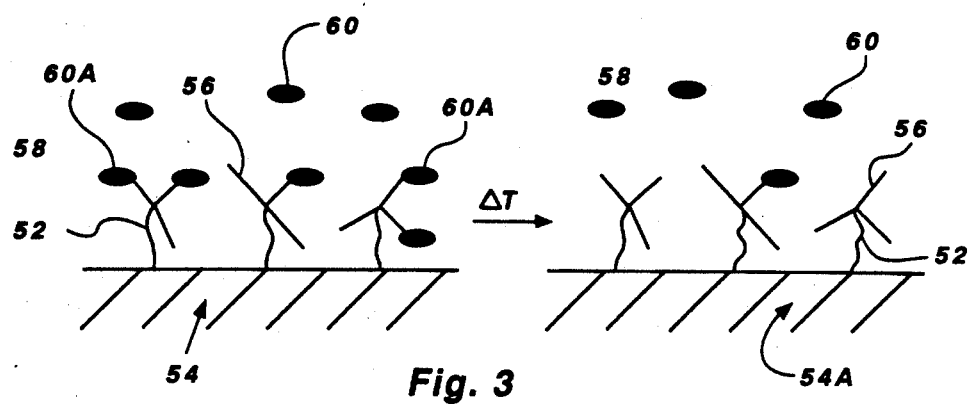

FIG. 3 depicts a third embodiment of the invention. In this embodiment, hydrophilic tethers 52 (e.g. a hydrophilic polymer capable of being attached to the substrate) are attached to the conductive substrate 54. Receptors, in the depicted case, moieties of an antibody-antigen complex 56, are bound to the hydrophilic tethers 52. When the temperatures of the surrounding ligand containing solution 58 and the conductive substrate 54 are the same, the ligands 60 bind the complementary moieties of an antibody-antigen complex 56. However, if a thermal pulse or other form of heat energy is conducted through the conductive substrate 54, thus increasing the temperature of the conductive substrate 54 relative to the surrounding ligand containing solution 58, the binding constant between the bonded ligand 60A and the complementary receptor (e.g. moiety of an antibody-antigen complex) 56 decreases thereby allowing the ligands 60 to dissociate from the moiety 56 back into the surrounding solution 58. See J. N. Herron, et al. *Biochemistry* 25 (1986) p. 4602.

Activation means for transmitting heat energy (i.e. a thermal pulse) through the conductive substrate 54 could be resistive heating of the conductive substrate 54, or by absorption of a near infrared beam by the solution at the interface of the conductive substrate 54 (e.g. an optical conduit) and the surrounding solution 58.

Temperatures useful in altering the binding of the ligand with the complementary receptors vary generally between 20° and 70° centigrade when the ligand receptor complex comprises some sort of natural product (e.g. moiety of an antibody-antigen complex). High temperatures tend to denature antibodies, lectins, enzymes, and other natural high affinity binding agents.

The ability to regulate and control specific binding and photosensitive polymers by an external source may have useful applications in information storage devices (e.g. "biochips"), bioorganic electronic devices, and optical devices (e.g. electric eyes).

Reference herein to specific details of certain embodiments is not intended to restrict the scope of the appended claims.

We claim:

1. A probe element capable of photon actuated chemical decoupling of a ligand comprising:
   a conductive substrate constructed so as to conduct photons;
   a plurality of first pendant molecules, each having a proximal end which is attached to said conductive substrate, and a distal end, wherein said distal end of each of said first pendant molecules has a coupling group attached thereto, said coupling group constructed so as to selectively couple to a ligand having a chemical structure capable of coupling to said coupling group;
   a plurality of second pendant molecules, each having a proximal end and a distal end, wherein said proximal end of each of said second pendant molecules is attached to said conductive substrate in proximity to at least one of said plurality of first pendant molecules, said second pendant molecules each having a first contracted conformation and a second extended conformation wherein said distal end of said second pendant molecules extends proximate to said coupling group of said first pendant molecules, said first contracted conformation existing when said second pendant molecules are in a substantially unenergized state and said second conformation existing when said second pendant molecules are subjected to a photon signal sufficient to extend said second pendant molecules from said first contracted conformation to said second extended conformation.

2. The probe element of claim 1 wherein said proximal end of each of said first pendant molecules is convalently bonded to said conductive substrate, and wherein said second extended conformation of said second pendant molecules causes dissociation of the ligand from said coupling group of said first pendant molecules.

3. The probe element of claim 2 wherein the photon signal is a wave of visble light and said second pendant molecules comprise photosensitive polymers.

4. The probe element of claim 1 wherein said conductive substrate comprises a planar waveguide.

5. The probe element of claim 1 wherein the coupling group of said first pendant molecules is a moiety of an antibody-antigen complex.

6. The probe element of claim 5 wherein said moiety of an antibody-antigen complex is an antibody.

7. The probe element of claim 5 wherein said moiety of an antibody-antigen complex is an antibody fragment.

8. The probe element of claim 5 wherein said moiety of an antigen-antibody complex is an antigen.

9. The probe element of claim 5 wherein said proximal end of each of said second pendant molecules is covalently bonded to said conductive substrate.

10. A method of externally regulating ligand-receptor binding comprising:
passing a solution containing ligands over a sensor comprising:
an optical conduit,
receptor molecules, each having a proximal end which is bonded to said optical conduit, and a distal end, wherein said distal end of each of said receptor molecules has a complexing site bonded thereto, said complexing site capable of complexing with said ligands, and
photoexpansive polymers bonded to said optical conduit and having free ends, interspersed among said receptor molecules, and having first and second conformations, wherein in said first conformation said free ends do not interfere with complexing of said ligand with said complexing site of said receptor molecules; and
transmitting light through said optical conduit to expand said photoexpansive polymers to said second conformation, wherein said free ends are extended proximate said complexing site of said receptor molecules to cause dissociation of said ligands from said receptor molecules.

11. An actuatable chemical coupling-decoupling device comprising:
a conductive substrate constructed so as to conduct a photon signal;
first pendant molecules each having a proximal end which is substantially immobilized upon said conductive substrate, and a free distal end, wherein said free distal end of each of said first pendant molecules has a coupling group attached thereto, said coupling group constructed so as to selectively couple to chemical compounds having a complementary site capable of coupling to said coupling group of said first pendant molecules;
second pendant molecules each having a proximal and a distal end, wherein said proximal end of each of said second pendant molecules is attached to said conductive substrate adjacent to said first pendant molecules, and having a first contracted conformation wherein said distal end of said second pendant molecules is remote from said free distal end of said first pendant molecules and a second extended conformation wherein said distal end of said second pendant molecules extends into the vicinity of said free distal end of said first pendant molecules;
sensing means for sensing a change in condition produced by the coupling of said chemical compounds to said coupling group of said first pendant molecules;
photo signal means interacting with said conductive substrate to photoactivate said second pendant molecules to said extended conformation to cause decoupling of said chemical compounds from said coupling group of said first pendant molecules.

12. A reuseable biosensor system comprising:
an optical conduit;
binding molecules each having a proximal end which is attached to said optical conduit, and a distal end, wherein said distal end of said binding molecules has a moiety of an antigen-antibody complex attached thereto, said moiety pendantly extending from said optical conduit and capable of binding a complementary moiety to form said antibody-antigen complex;
photosensitive polymers each having a first end which is attach to said optical conduit at a point proximate said binding molecules, and a second end which is free, said photosensitive polymers having a first contracted unstimulated conformation existing when said photosensitive polymers are subjected to quanta of light in less than the amount required for stimulation, and a second extended conformation existing when a stimulating quanta of light is transmitted through said optical conduit, said photosensitive polymers being of sufficient length that when said second conformation exists, said second end of said photosensitive polymers extends proximate said moiety of an antibody-antigen complex at said distal end of said binding molecules;
a photon source constructed so as to transmit photons through said optical conduit and interacting with said optical conduit; and
sensing means operably disposed to interact with said optical conduit for sensing the presence or absence of said antigen-antibody complex on said binding molecules.

13. A probe element capable of photon actuated chemical coupling-decoupling of a ligand comprising:
a conductive substrate constructed so as to conduct a photon signal;
a plurality of first pendant molecules each having a proximal end which is attached to said conductive substrate, and a distal end, wherein said distal end of each of said first pendant molecules has a coupling group attached thereto, said coupling group constructed so as to selectively couple to chemical compounds having a complementary site;
a plurality of second pendant molecules each having a proximal end which is attached to one of said first pendant molecules, and a distal end, said second pendant molecules having a first contracted conformation and a second extended conformation wherein said distal end of said second pendant molecules extends proximate to said coupling group of said first pendant molecules and interferes with binding of said chemical compounds to said coupling group, said first contracted conformation existing when no photon signal is conducted through said conductive substrate and said second conformation existing when said second pendant molecules are subjected to a photon signal to extend said second pendant molecules from said first contracted conformation to said second extended conformation.

14. The probe element of claim 13 wherein the photon signal is a wave of light and said second pendant molecules comprise photoexpansive polymers.

15. The probe element of claim 14 wherein said conductive substrate comprises a planar waveguide.

16. The probe element of claim 14 wherein the coupling group of said first pendant molecules is a moiety of an antibody-antigen complex.

17. The probe element of claim 16 wherein said moiety of an antibody-antigen complex is an antibody.

18. The probe element of claim 16 wherein said moiety of an antibody-antigen complex is an antibody fragment.

19. The probe element of claim 16 wherein said moiety of an antibody-antigen complex is an antigen.

20. The probe element of claim 13 wherein said first pendant molecules are antifluorescein antibodies.

21. A probe element capable of thermally-actuated chemical coupling-decoupling of a ligand comprising:
a conductive substrate constructed so as to conduct a thermal energy pulse;
a plurality of pendant hydrophilic molecules each having a proximal end which is attached to said conductive substrate, and a distal end; and
a plurality of pendant receptor molecules each having a proximal end which is attached to one of said pendant hydrophilic molecules, and a distal end, wherein said distal end of each of said pendant receptor molecules has a coupling group attached thereto, said coupling group constructed so as to selectively couple to chemical compounds having a complementary coupling moiety capable of reversibly binding to said coupling group to form a complex, said complex being thermally sensitive to decouple said complementary coupling moiety from said coupling group when the thermal energy pulse is transmitted through said conductive substrate.

22. The probe element of claim 21 wherein said proximal end of each of said pendant hydrophilic molecules is covalently bonded to said conductive substrate.

23. The probe element of claim 22 wherein said thermal pulse is of a wave of near infrared light and said conductive substrate is an optical conduit capable of transmitting said wave of near infrared light.

24. The probe element of claim 22 wherein said conductive substrate is a heat conducting metallic strip.

25. The probe element of claim 23 wherein said coupling group of each of said pendant receptor molecules is a moiety of an antibody-antigen complex.

26. A probe element capable of thermally actuated decoupling of a ligand, comprising:
a conductive substrate constructed so as to conduct a thermal signal;
a plurality of pendant molecules each having a proximal end which is attached to said conductive substrate via a tethering compound, and a distal end, wherein said distal end of each of said pendant molecules has a coupling group attached thereto, said coupling group constructed so as to selectively couple to chemical compounds having a complementary coupling moiety capable of reversibly binding to said coupling group to form a complex, said complex being thermally sensitive to decouple said complementary coupling moiety from said coupling group when the thermal signal is transmitted through said conductive substrate.

27. The probe element of claim 26, wherein said conductive substrate is further constructed to conduct a thermal signal of magnitude sufficient to cause said coupling group to reach a decoupling temperature between about 20° C. and about 70° C.

28. The probe element of claim 26, wherein said pendant molecules comprise moieties of an antigen-antibody complex.

29. A probe element capable of decoupling of a ligand in response to change in temperature of the element, comprising:
a conductive substrate constructed so as to conduct a thermal signal;
a plurality of pendant molecules each having a proximal end which is attached to said conductive substrate, and a distal end, wherein said distal end of each of said pendant molecules has a coupling group attached thereto, said coupling group constructed so as to selectively couple to chemical compounds having a complementary coupling moiety capable of reversibly binding to said coupling group to form a complex, said complex being thermally sensitive to decouple said complementary coupling moiety from said coupling group when the thermal signal is transmitted through said conductive substrate.

30. The probe element of claim 29 wherein said conductive substrate is an optical conductor and the thermal signal is infrared light.

31. The probe element of claim 30 wherein said pendant molecules are derived from antifluorescein antibodies.

32. The probe element of claim 29 wherein said conductive substrate is a metallic strip and the thermal signal is a resistive heat pulse.

33. The probe element of claim 32 wherein said pendant molecules comprise antifluorescein antibodies.

* * * * *